United States Patent [19]

Erlemann et al.

[11] Patent Number: 4,833,259

[45] Date of Patent: May 23, 1989

[54] LIGHT SCREENING AGENTS

[75] Inventors: Gustav Erlemann, Basel, Switzerland; Christian Fizet, Zimmersheim, France; Horst Pauling, Bottmingen, Switzerland

[73] Assignee: Hoffmann-La Roche Inc., Nutley, N.J.

[21] Appl. No.: 88,332

[22] Filed: Aug. 24, 1987

[30] Foreign Application Priority Data

Sep. 15, 1986 [CH] Switzerland ................ 3696/86
Jul. 16, 1987 [CH] Switzerland ................ 2714/87

[51] Int. Cl.$^4$ .............. A61K 7/44; C07C 69/76; C07D 307/26
[52] U.S. Cl. ................ 549/318; 424/60; 514/873; 549/407; 560/55

[58] Field of Search ........... 560/55; 549/407, 318; 514/873

[56] References Cited

U.S. PATENT DOCUMENTS

| | | | |
|---|---|---|---|
| 2,251,287 | 8/1941 | Lott | 560/55 |
| 2,310,973 | 2/1943 | Lott | 560/55 |
| 2,545,439 | 3/1951 | Allen et al. | 560/55 |

FOREIGN PATENT DOCUMENTS 0166221 1/1986 European Pat. Off. ......... 424/60

*Primary Examiner*—Dale R. Ore
*Attorney, Agent, or Firm*—Jon S. Saxe; George M. Gould; William H. Epstein

[57] ABSTRACT

The novel sunscreen agents which are esters, namely esters of p-methoxy-cinnamic acid with d,1-α-tocopherol, pantolactone or panthenol.

5 Claims, No Drawings

LIGHT SCREENING AGENTS

SUMMARY OF THE INVENTION

The invention is concerned with novel light screening agents which are p-methoxy-cinnamic acid esters of the formula:

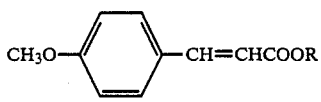

wherein R is the alcohol residue of d,l-α-tocopherol, pantolactone or panthenol, whereby panthenol can be esterified once, twice or three times, and a process for their manufacture.

DETAILED DESCRIPTION

The terms "pantolactone" and "panthenol" are intended to embrace the <R> and the <R,S>-forms.

The esters of formula I absorb the erythema-producing ultraviolet rays of the sun (between 270 and 300 mμ), i.e. they keep these rays away from the living epidermis cells. Consequently, the esters of the formula I can be used as light screening agents. The invention is accordingly also concerned with a process for the manufacture of a light screening composition, which process comprises incorporating a compound of formula I into a base which is usual in cosmetics. Further, the invention is concerned with a light screening composition which contains a compound of formula I and finally with the use of the compounds I as light screening agents.

The compounds I can be obtained in accordance with the invention by esterifying a reactive derivative of p-methoxycinnamic acid, especially the chloride, in a manner known per se.

The starting materials are conveniently used in pure form.

The esterification is carried out in a manner known per se using a reactive derivative, e.g. the anhydride or—preferably—a halide, especially the chloride. The esterification is conveniently carried out in the presence of tertiary amines such as e.g. pyridine, triethylamine or N,N-dimethylaniline. The addition of a solvent, e.g. a (chlorinated) hydrocarbon or a lower ester, is convenient.

The compound of formula I where R is H can be utilized to esterfy on any one of the free hydroxy groups on panthenol. Since panthenol has three free hydroxy groups, the compound of formula I where R is H can be a mono, di or tri ester of panthenol.

In utilizing the compounds of formula I to form a light screening agent, the compound of formula I can be incorporated with any conventional cosmetically acceptable carrier for topical administration. Generally the carrier comprises a plurality of cosmetically acceptable substances. Any conventional cosmetically acceptable substance can be used to formulate the compound of formula I into a light screening composition for topical administration.

Any usual preparation which corresponds to the cosmetic requirements, e.g. oils, creams, lotions, emulsions, salves, gels, solutions, sprays, sticks and the like, can serve as the cosmetic base. The light screening effect is, of course, dependent on the base which is used. Further, the intensity of the light screening effect depends on the active substance concentration in the case of the same base. Suitable concentrations are e.g. between 1–6%, preferably between 3–5%, in the cosmetic preparations.

The substances in accordance with the invention can also be combined with other usual light screening agents, in which case a potentiation of the light screening effect, i.e. a synergistic effect, can occur.

Furthermore, the pronounced skin compatibility of the novel esters or worthy of mention.

An additional valuable property of the compounds I lies in the fact that they accelerate the epithelialization of superficial wounds and therefore, quite generally, promote wound healing. This fact is accordingly of significance, because often insufficient sunscreen agent is applied by the user or a sunscreen preparation having an inadequate sunscreen factor is used. A sunburn subsequently results. In such cases the compounds I accelerate the abatement of the sunburn quite markedly.

The influencing of the epithelialization and wound healing was determined using the following methodology:

A wound healing model which permits the evaluation of the epithelialization and healing of superficial wounds was developed. The good reproducibility of the method becomes evident from repeated comparisons between placebo and preparations containing D-panthenol as the active substance.

MATERIAL

A gel of the following composition with and without the panthenol triester of p-methoxycinnamic acid was prepared for the investigations:

PLACEBO

| | |
|---|---|
| Pluronic L 62 (emulsifier) | 10.00 g |
| Lecithin for mixed micelles (in order to produce a homogeneous gel) | 0.50 g |
| Aerosil 200 (SiO$_2$; consistency provider) | 8.00 g |
| Medium chain triglyceride (gel former) | 81.50 g |
| | 100.00 g |

PLACEBO WITH THE PANTHENOL TRIESTER OF P-METHOXYCINNAMIC ACID

| | |
|---|---|
| Panthenol triester of p-methoxycinnamic acid | 1.00 g |
| Pluronic L 62 | 10.00 g |
| Lecithin for mixed micelles | 0.50 g |
| Aerosil 200 | 8.00 g |
| Medium chain triglyceride | 80.50 g |
| | 100.00 g |

EXPERIMENTAL ANIMALS AND THE MAINTENANCE OF THE ANIMALS

The wound healing experiment was carried out with male Füllinsdorf albino rats of the SPF breed from the Institut für biologisch-medizinische Forschung AG, 4414 Füllinsdorf. Their average weight on arrival in the laboratory amounted to about 200 g. The animals were kept in individual cages under perfectly hygenic conditions and protected from draughts.

FEED RATIONS

In order to eliminate the influence of vitamin additives on wound healing, a semi-synthetic feed corresponding to the requirements of standard rat feed was prepared. The feed rations contained 12.6 MJ of utilizable energy per kg and 17% of digestible raw albumin. Pelletted rat feed NAFAG 854 (Nafag Nähr- und Futternittel AG, 9202 Gossau) was administered in the case of tests with the topical preparations.

BLISTER TECHNIQUE

In order that the progress of the healing can be tested with the topical use of the preparations, sucking discs were used to produce intraepidermal wounds. By means of the disposition of the sucking discs one wound was placed on each of the two sides of the linea alba at a distance of 20 mm and with an area of 12.6 mm$^2$. A common vacuum conduit provided identical conditions in the sucking discs. The vacuum was produced by a hand pump (Dermovac, Firma Instrumentarium, Helsinki, Finland) and was controlled or regulated by a manometer and needle valve. After a vacuum of 100 mg Hg column for one hour there resulted a blister, whose content was obtained with the aid of a Pasteur pipette for analytical purposes. Thiogenal R for animals, an excitation-free thiobarbiturate from the firm Merck GmbH, Darmstadt, was used for the anaesthesis.

VAPOUR PRESSURE MEASUREMENT

The serious fluid on the wound surface was measured with the aid of rapidly responding sensors. Three sensors in a measuring head were provided for the simultaneous measurement of an intact skin position (above the xiphoid) and the two wound areas. In order to obtain identical initial conditions for all three measurement positions, the chambers, after positioning, were adjusted to 15% residual moisture with a stream of air dried over molecular sieve. The vapour pressure saturation curves of the three measurement positions were registered independently of one another on a 3-channel continuous line recoring instrument. The measurement period amounted in each case to exactly 2½ minutes with a paper feed throughput of 4 cm/min. The relative vapour output was determined from the circuit recordings by in each case determining the distance of the curve segments for the two wound areas and correcting by the measured value at the intact skin position.

The application of the preparation (left ventral side) and placebo (right) was effected daily following the measurement procedure. 0.75 mg of the respective formulation per wound area was finely distributed with a small spatula. Short acting inhalation narcosis with Halothane R from the Firm Hoechst, Frankfurt, was sufficient for the rapid measurement precedure.

STATISTICAL EVALUATION OF THE MEASUREMENT RESULTS

In order that the progress of the healing can be followed better, the first measurement values obtained during the settling of the wound were fixed at 100%. The results of one group obtained at each point in time were used to form average values and standard errors. The linear regression calculation was used in that the time up to complete wound closure could be given. The healing period in hours is expressed by the x-axis intercept which results upon intersection of the regression lines with the abscissa. The efficacy of the experimental cream, which corresponds to the acceleration of the progress of the healing, was determined by calculating the quotient from the x-axis intercepts.

RESULTS

The action of the addition of the panthenol triester of p-methoxycinnamic acid on the epithelialization of superficial wounds could be determined without problems on the basis of the experiment. Compared with the placebo, the gel with a 1% addition of the panthenol triester of p-methoxycinnamic acid exhibited a significant acceleration of the epithelialization with a factor 1.3.

The panthenol di- and monoester showed an analogous behavior.

In the following Examples the temperatures are given in degrees Celsius.

EXAMPLE 1

16.3 g of <R>-pantolactone (0.125 mol) and 28 g of 4-methoxycinnamic acid chloride (about 0.14 mol) are placed in 170 ml of CH$_2$Cl$_2$ while gassing with argon in a 350 ml 4-necked sulphonation flask provided with a thermometer, a reflux condenser, a magnetic stirrer as well as a 20 ml dropping funnel. A solution of 11 g (0.139 mol) of pyridine in 30 ml of CH$_2$Cl$_2$ is now added dropwise within 30 minutes, whereby the temperature rises slowly. The reaction mixture is finally heated to reflux temperature for 3 hours. The reaction mixture is washed with 150 ml of water, 2× with 40 ml of 5% HCl, 2× with 40 ml of 5% NaHCO$_3$ and 1× with 100 ml of water. The organic phase is separated and dried over Na$_2$SO$_4$. The solvent is removed on a rotary evaporator. The thus-obtained crude product is recrystallized from 100 ml of ethyl acetate/hexane (60:100). There are obtained 33.6 g of white crystals of the <R>-pantolactone ester of p-methoxycinnamic acid (yield 92.6%).

EXAMPLE 2

34.8 g of the above ester (0.12 mol) and 13.5 g of 3-aminopropanol (0.18 mol) are suspended or dissolved in 100 ml of MeOH while gassing with argon in a 250 ml 4-necked sulphonation flask provided with a thermometer and a magnetic stirrer. The reaction mixture becomes clear after about 30 minutes. It is stirred at reflux temperature for 3 hours. The methanol is evaporated on a rotary evaporator and the residue is dissolved in 350 ml of CH$_2$Cl$_2$. This solution is washed with 2× 60 ml of water. The organic phase is separated, dried over Na$_2$SO$_4$ and concentrated on a rotary evaporator. The yellow, viscous residue (41.5 g) is chromatographed (ethyl acetate/acetonitrile, 5:5) on 1 kg of silica gel (0.040–0.063 mm) under 0.5 bar pressure. There are obtained 33.1 g of slightly yellow coloured <R>-panthenol monoester of p-methoxycinnamic acid (yield 75.4%).

EXAMPLE 3

11.3 g of D-panthenol (0.055 mol) are placed in 100 ml of THF while gassing with argon in a 500 ml 4-necked sulphonation flask provided with a thermometer, a 100 ml dropping funnel, a magnetic stirrer and a reflux condenser. A solution of 27.8 g of 4-methoxycinnamic acid chloride (0.14 mol) in 100 ml of tetrahydrofuran is then added dropwise within about 15 minutes. A solution of 11.1 g of pyridine (0.14 mol) is now added dropwise within about 30 minutes and the mixture is stirred for a further 3 hours. The precipitate is filtered off under suction and the filtrate is concentrated on a rotary evaporator. The residue is dissolved in 300 ml of CH$_2$Cl$_2$. This solution is washed with 2× 60 ml of 5% HCl and then with 2× 60 ml of 5% NaHCO$_3$. After drying (Na$_2$SO$_4$) the organic phase is concentrated on a rotary evaporator. The yellow, viscous residue (33.8 g) is chromatographed (toluene/ethyl acetate, 8:2) on 1 kg of silica gel (0.04–0.063 mm) under 0.5 bar pressure. There are obtained 15.9 g of yellowish <R>-panthenol diester of p-methoxycinnamic acid (yield 55%).

EXAMPLE 4

17.4 g of D-panthenol )0.085 mol) are placed in 300 ml of methyl acetate while gassing with argon in a 750 ml 4-necked sulphonation flask provided with a thermometer, a 100 ml dropping funnel, a magnetic stirrer and a reflux condenser. A solution of 75.5 g of 4-methoxycinnamic acid chloride (0.38 mol) in 150 ml of methyl acetate is then added dropwise within about 20 minutes. A solution of 33.6 g of pyridine (0.425 mol) is added dropwise within about 40 minutes. The reaction mixture is finally heated to reflux temperature for 4 hours. After cooling the precipitate is filtered off under suction. The filtrate is washed with 2× 150 ml of 5% HCl and then with 2× 100 ml of water. After drying over Na$_2$SO$_4$ the organic phase is concentrated on a rotary evaporator. The yellow, viscous residue (74.2 g) is chromatographed (toluene/ethyl acetate, 7:1) on 1 kg of silica gel (0.040–0.063 mm) under 0.5 bar pressure. There are obtained 50.1 g of yellow <R>-panthenol triester of p-methoxycinnamic acid (yield 86%).

EXAMPLE 5

4.3 g of dl-α-tocopherol (0.010 mol) and 1.34 g of pyridine (0.017 mol) are placed in 20 ml of CH$_2$Cl$_2$ while gassing with argon in a 100 ml 4-necked sulphonation flask provided with a temperature, a 20 ml dropping funnel, a magnetic stirrer and a reflux condenser. A solution of 0.95 g of 4-methoxycinnamic acid chloride (0.015 mol) in 15 ml of CH$_2$Cl$_2$ is added dropwise within 10 minutes. The reaction mixture is heated to reflux temperature for 3 hours. The solution is washed in succession with 10 ml of water, 10 ml of 5% HCl and 10 ml of 5% NaHCO$_3$. After drying (Na$_2$SO$_4$) the solvent is concentrated on a rotary evaporator. The crude product (6.3 g) is chromatographed (toluene) on 150 g of silica gel (0.040–0.063 mm) under 0.5 bar pressure. There are obtained 5.2 g of yellowish d,l-α-tocopherol ester of p-methoxycinnamic acid (yield 88%).

EXAMPLE 6

A. SUNSCREEN LOTION

|   |   | Parts by weight |
|---|---|---|
| A. | Panthenol diester of p-methoxycinnamic acid | 4.00 |
|   | Isopropyl myristate | 3.00 |
|   | Stearic acid | 3.00 |
|   | Almond oil | 2.50 |
|   | Hexyl laurate | 8.00 |
|   | Dimethicone (silicon oil) | 1.00 |
|   | Vit. E acetate | 1.00 |
| B. | Diethanolamine cetyl phosphate | 4.00 |
| C. | Allantoin | 0.30 |
|   | Water | 73.20 |
| D. | Perfume, preservative | q.s. |

A is heated to 85° while stirring. Subsequently, B is dissolved in A. Then, C is heated to 70° and added to A+B while stirring. The mixture is cooled slowly wile stirring and D is added at 40°. The mixture is stirred further until room temperature is reached.

B. WATER-RESISTANT SCREENING CREAM (O/W EMULSION)

|   |   | Parts by weight |
|---|---|---|
| A. | Panthenol monoester of p-methoxycinnamic acid | 2 |
|   | ARLACEL 481 (sorbitan sequioleate, glycerol oleate and beeswax) | 9 |
|   | Lanolin | 1 |
|   | Paraffin oil | 8 |
|   | Vit. E acetate | 2 |
| B. | Aluminium stearate | 0.1 |
|   | Isopropyl myristate | 10.00 |
| C. | Magnesium stearate | 0.3 |
|   | Propylene glycol | 3 |
|   | Water | 64.60 |
| D. | Perfume and preservative | q.s. |

A is dissolved at 85° while stirring. B is dissolved at 80° and incorporated into A. C is heated to 70° and added while stirring to the mixture A+B. The mixture is cooled slowly and D is incorporated at 40° while stirring. The mixture is stirred further until room temperature is reached.

C SUNSCREEN CREAM (O/W EMULSION)

|   |   | Parts by weight |
|---|---|---|
| A. | Panthenol triester of p-methoxycinnamic acid | 3 |
|   | Vit. E acetate | 2 |
|   | Stearic acid | 10 |
|   | Cetyl alcohol | 1 |
|   | Glycerol monomyristate | 5 |
|   | Isopropyl myristate | 7 |
|   | Oleyl alcohol | 4 |
| B. | Diethanolamine cetyl phosphate | 3 |
| C. | Water | 58 |
|   | Panthenol | 1 |
|   | Propylene glycol | 6 |
|   | Perfume, preservative | q.s. |

The combined components of A are heated on a water bath and thereupon B is added at this temperature. The mixture C is heated to 75° and added to A+B. After cooling to 25°–30° any loss of water is compensated for.

D. LIQUID SUNSCREEN OIL

|   | Parts by weight |
|---|---|
| Pantolactone ester of p-methoxycinnamic acid | 5 |
| Ethyl alcohol | 20 |
| Oleyl alcohol | 30 |
| Isopropyl myristate | 35 |
| Vit. E acetate | 1 |
| Cetiol (decyl oleate) | 9 |
|   | 100 |

E. SUNSCREEN STICK

|   | Parts by weight |
|---|---|
| Pantolactone ester of p-methoxycinnamic acid | 1 |
| Panthenol triester of p-methoxycinnamic acid | 4 |

| -continued | |
|---|---|
| | Parts by weight |
| CORHYDROL 1/35 (hydrogenated castor oil) | 15 |
| Oleyl alcohol | 20 |
| Texwax MH/81 (microcrystalline wax) | 30 |
| Mineral oil | 20 |
| Vaseline | 10 |

The components are melted at 80° while stirring and cooled slowly. The mass is poured into the desired forms at 40°.

We claim:

1. A p-methoxy-cinnamic acid ester of the formula

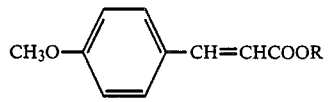

wherein R is the alcohol residue of d,l-α-tocopherol, pantolactone or panthenol, whereby panthenol can be esterfied once, twice or three times.

2. The ester of claim 1 wherein said ester is d,l-α-Tocopherol ester of p-methoxy-cinnamic acid.

3. The ester of claim 1 wherein said ester is pantolactone ester of p-methoxy-cinnamic acid.

4. The ester of claim 1 wherein said ester is panthenol diester of p-methoxy-cinnamic acid.

5. The ester of claim 1 wherein said ester is panthenol triester of p-methoxy-cinnamic acid.

* * * * *